United States Patent
Hwang et al.

(10) Patent No.: US 11,766,460 B2
(45) Date of Patent: Sep. 26, 2023

(54) PHARMACEUTICAL COMPOSITION COMPRISING AMNIOTIC FLUID STEM CELL SPHEROID AND THE USE THEREOF IN TREATMENT OF URINARY INCONTINENCE

(71) Applicant: U-Neuron Biomedical Inc., New Taipei (TW)

(72) Inventors: Shiaw-Min Hwang, Taipei (TW); Shing-Hwa Lu, Taipei (TW); Kuei-Chang Li, Taipei (TW); Wei-Ti Wang, Taipei (TW)

(73) Assignee: U-NEURON BIOMEDICAL INC., New Taipei (TW)

( * ) Notice: Subject to any disclaimer, the term of this patent is extended or adjusted under 35 U.S.C. 154(b) by 30 days.

(21) Appl. No.: 17/117,967

(22) Filed: Dec. 10, 2020

(65) Prior Publication Data
US 2022/0079996 A1    Mar. 17, 2022

(30) Foreign Application Priority Data
Sep. 11, 2020 (CN) .......................... 202010951931.5

(51) Int. Cl.
| | |
|---|---|
| *A61K 35/50* | (2015.01) |
| *A61K 9/48* | (2006.01) |
| *A61K 31/728* | (2006.01) |
| *A61P 13/02* | (2006.01) |

(52) U.S. Cl.
CPC ............ *A61K 35/50* (2013.01); *A61K 9/4808* (2013.01); *A61K 31/728* (2013.01); *A61P 13/02* (2018.01)

(58) Field of Classification Search
None
See application file for complete search history.

(56) References Cited

U.S. PATENT DOCUMENTS

| | | | | |
|---|---|---|---|---|
| 5,700,783 | A * | 12/1997 | Pinto .................... | A61L 24/106 514/13.6 |
| 2015/0196604 | A1 * | 7/2015 | Lim ....................... | A61K 35/50 424/93.7 |
| 2017/0106050 | A1 * | 4/2017 | Williams ................. | A61P 1/04 |
| 2021/0309962 | A1 * | 10/2021 | Young ................. | C12N 5/0605 |

OTHER PUBLICATIONS

Loukogeorgakis et al. "Concise Review: Amniotic Fluid Stem Cells: The Known, the Unknown, and Potential Regenerative Medicine Applications" 2016.*
Miceli et al. "Comparison of Immunosuppressive and Angiogenic Properties of Human Amnion-Derived Mesenchymal Stem cells between 2D and 3D Culture Systems". 2019.*
Razian et al. "Production of Large Numbers of Size-controlled Tumor Spheroids Using Microwell Plates" 2013.*
"Drug Screening and Phenotypic Analysis in a Microwell-Based 3D Cell Culture System" 2019. https://www.stemcell.com/webinar-drug-screening-and-phenotypic-analysis-in-a-microwell-based-3d-cell-culture-system.html.*
"Ultra-High Throughput Production of Spheroids with Aggrewell".*

\* cited by examiner

*Primary Examiner* — Danah Al-Awadi
(74) *Attorney, Agent, or Firm* — Birch, Stewart, Kolasch & Birch, LLP

(57) ABSTRACT

Disclosed herein is a use of an amniotic fluid stem cell spheroid in the preparation of a composition or pharmaceutical composition for treating urinary incontinence, wherein said pharmaceutical composition may further comprise hyaluronic acid.

2 Claims, 3 Drawing Sheets

PHARMACEUTICAL COMPOSITION COMPRISING AMNIOTIC FLUID STEM CELL SPHEROID AND THE USE THEREOF IN TREATMENT OF URINARY INCONTINENCE

FIELD OF THE INVENTION

The present invention relates to a method for the treatment of urinary incontinence, comprising administering an effective amount of amniotic fluid stem cells to a patient; specifically, administering an effective amount of amniotic fluid stem cells and hyaluronic acid to the patient.

BACKGROUND OF THE INVENTION

Amniotic fluid cells are used as a routine prenatal diagnosis to detect whether the fetal chromosomes are abnormal. In addition, studies have shown that some small nucleated cells with the characteristics of hematopoietic progenitor cells can be identified in the amniotic fluid before 12 weeks of pregnancy, suggesting that these cells may come from yolk sac. There were reports from 2004 to 2006 of successful isolation and identification of existence of another group of stem cells in amniotic fluid. It has proven that these amniotic fluid stem cells express specific biomarkers of both mesenchymal stem cells and neural stem cells, with the ability of differentiating into bones, cartilage, fat, and nerve cells. Amniotic fluid stem cells can proliferate stably in large quantities in vitro, and they proliferate faster than mesenchymal stem cells obtained from adult bone marrow and fat, without the tumorigenic potential of embryonic stem cells. Therefore, amniotic fluid stem cells have the potential of application to clinical medicine.

The current treatment methods for urinary incontinence can be roughly divided into physical rehabilitation and surgical treatment. The effect of physical rehabilitation is limited. Although surgical treatment has a high success rate, it is less effective in male population, and some patients refuse to have surgery. Therefore, there is still an urgent need for a simple and effective therapy to treat urinary incontinence.

SUMMARY OF THE INVENTION

An aspect disclosed herein is a method for the treatment of urinary incontinence, comprising administering to a subject in need a pharmaceutical composition including a therapeutically effective amount of amniotic fluid stem cells.

In a particular embodiment, the pharmaceutical composition further comprises hyaluronic acid.

In a particular embodiment, the amniotic fluid stem cells are amniotic fluid stem cell spheroids.

In a particular embodiment, the therapeutically effective amount is 500-50,000 amniotic fluid stem cells/µl.

In a particular embodiment, each of the amniotic fluid stem cell spheroids comprises 50-250 amniotic fluid stem cells.

Another aspect disclosed herein is a pharmaceutical composition for the treatment of urinary incontinence, comprising:
a therapeutically effective amount of amniotic fluid stem cells;
hyaluronic acid; and
a pharmaceutically acceptable carrier.

In a particular embodiment, the pharmaceutical composition further comprises hyaluronic acid.

In a particular embodiment, the pharmaceutical composition comprises 500-50,000 amniotic fluid stem cells/µl.

In a particular embodiment, each of the amniotic fluid stem cell spheroids comprises 50-250 amniotic fluid stem cells.

BRIEF DESCRIPTION OF THE DRAWINGS

The foregoing summary, as well as the following detailed descriptions of the invention, will be better understood when read in conjunction with the appended drawings. In the drawings.

DESCRIPTION OF THE INVENTION

Figure 1:
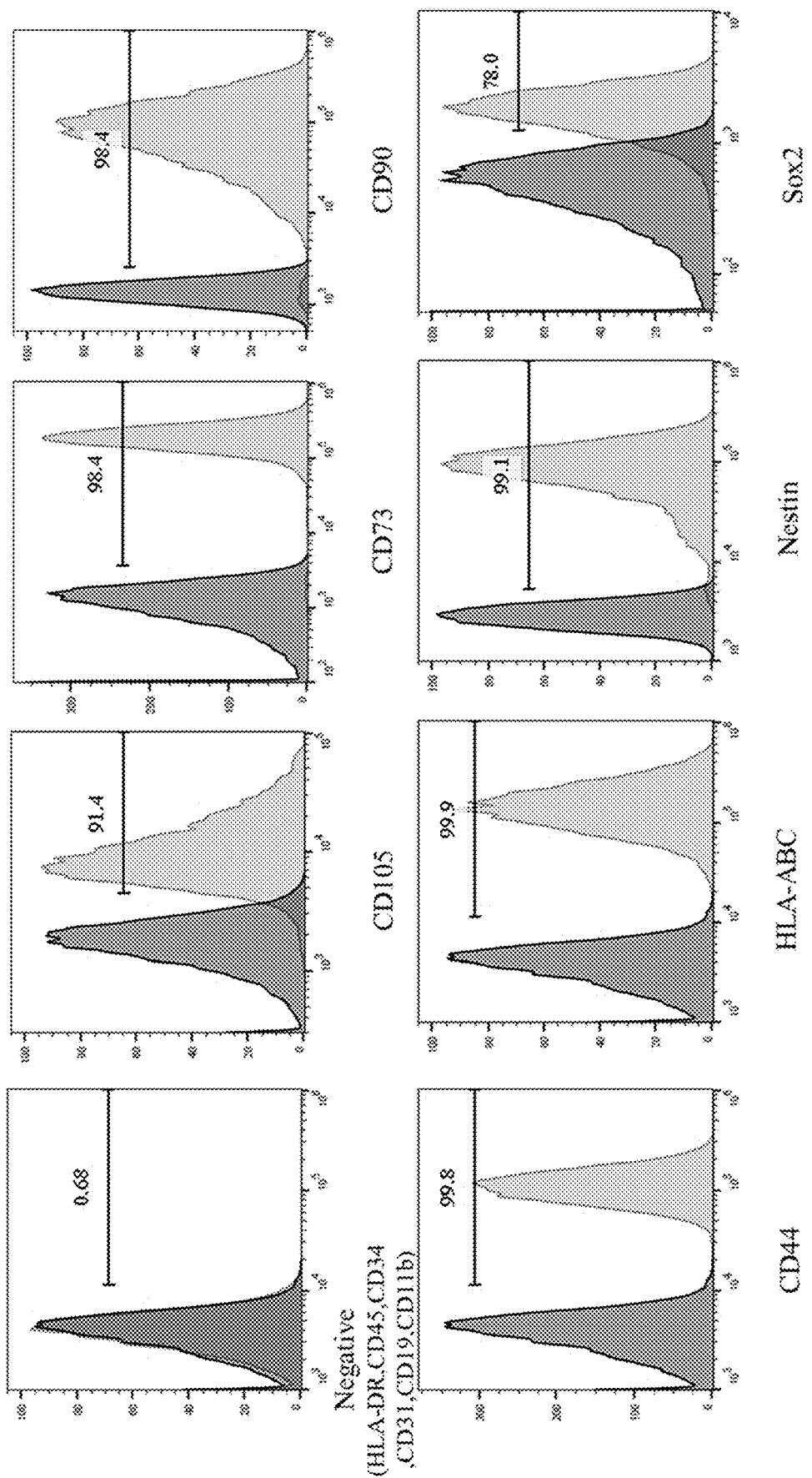
FIG. 1 shows the results of analysis of the expression ratio of the cell surface markers of amniotic fluid stem cells. The cell surface markers include CD29, CD44, CD73, CD90, and CD105, as well as HLA-ABC, nestin, and sox2.

The following embodiments when read with the accompanying drawings are made to clearly exhibit the above-mentioned and other technical contents, features and effects of the present disclosure. Through the exposition by means of the specific embodiments, people would further understand the technical means and effects of the present disclosure adopted to achieve the above-indicated objectives. Moreover, as the contents disclosed herein can be readily understood and implemented by a person skilled in the art, all equivalent changes or modifications which do not depart from the concept of the present disclosure shall be encompassed by the appended claims.

Unless otherwise defined, all the technical and scientific terms used herein have the same definition as commonly understood by a person of ordinary skills in the art to which the present disclosure pertains. As used in the specification and the appended claims, the singular forms "a," "an" and "the" include plural referents unless the context clearly dictates otherwise. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described. Unless otherwise specified, all the material used herein is commercial and can be easily obtained.

The term "about" used herein refers to a measured quantity, such as dose, including the deviation ±15% or ±10% relative to a specified quantity in an embodiment; the deviation ±5% relative to a specified quantity in a preferred embodiment; the deviation ±1% relative to a specified quantity in a further preferred embodiment; or the deviation ±0.1% relative to a specified quantity in a most preferred embodiment; whereas the nature of the substance the quantity pertains to is not affected thereby.

The term "urinary incontinence" used herein refers to involuntary leakage of urine, which can be divided into many types based on its symptoms, including: urge incontinence, stress incontinence, overflow incontinence, functional incontinence, and mixed incontinence, which refers to a combination of the above types of urinary incontinence.

Typical symptoms of urge incontinence include sudden, frequent, and difficult-to-stop the desire to urinate, causing the patient to be unable to control micturition. Urge incontinence is caused by bladder nerve damage, nervous system damage, or muscle damage, and is usually a complication of brain diseases such as stroke, Parkinson's disease, or Alzheimer's disease.

The typical symptom of stress incontinence includes a small amount of urine leakage caused by a patient's coughing, sneezing, heavy lifting, or pressure on the abdominal cavity during exercise. Stress incontinence is usually caused by weak pelvic floor muscles.

The typical symptom of overflow incontinence includes a small amount of urine leakage caused by the pressure within the bladder exceeding the urethral resistance or weak bladder muscle contractions.

Functional incontinence refers to the fact that an individual cannot move to the toilet to urinate due to their physical restriction caused by diseases, such as stroke, dementia, mental illness, of the individual, and is unrelated to physical disorders of the bladder.

Symptoms of urinary incontinence also include overactive bladder, which is caused by involuntary contractions of the detrusor muscle when the bladder is full. Typical symptoms of overactive bladder include frequent urination and nocturia.

Interstitial cystitis is a condition related to urinary incontinence, which is caused by chronic bladder inflammation. The causes of interstitial cystitis include autoimmune diseases, allergies, or infectious diseases. Typical symptoms of interstitial cystitis include frequent urination, sleep enuresis, suprapubic pain (including bladder, pelvis, and perineum), or dyspareunia.

The term "treatment" used herein includes, by treatment or prevention, alleviating, reducing, or improving at least one symptom or physical condition, preventing new symptoms, inhibiting diseases or physiological conditions, preventing or slowing the development of a disease, causing recovery of a disease or physical condition, ameliorate physiological conditions caused by a disease, and stopping symptoms or physiological conditions.

Therefore, the term "treatment" used herein refers to improving, alleviating, or reversing the symptoms of urinary incontinence, reducing the risk of developing urinary incontinence, inhibiting the progression of urinary incontinence, or preventing urinary incontinence.

The term "pharmaceutical composition" used herein refers to a mixture of a therapeutically effective amount of amniotic fluid stem cells and other ingredients, including stabilizers, diluents, dispersants, suspending agents, thickening agents, or excipients, or combinations thereof.

The term "effective amount" or "therapeutically effective amount" used herein refers to a sufficient amount of a compound or drug that can relieve one or more symptoms or physiological conditions after the patient takes the compound or drug, which results in reducing and/or alleviating symptoms, conditions, or causes, or other physiological changes. For example, the "effective amount" for treatment includes a dose of the compound provided by the present invention that can significantly reduce the symptoms of the disease clinically. An appropriate effective amount depends on common pharmaceutical techniques, such as dose escalation methods.

The term "pharmaceutically acceptable" used herein refers to the situation in which within the scope of reasonable medical judgment, a drug is suitable for use in contact with a tissue of a subject (such as a human) taking the drug, without excessive toxicity, irritation, allergic reaction, or other problems or complications, and with reasonable benefit/risk ratio. Each carrier must be compatible with other ingredients in order to be "acceptable".

The term "carrier" used herein, such as a solid, liquid, or semi-solid carrier, refers to a non-toxic compound or agent that has the function of assisting cells or tissues to absorb drugs.

The carrier is selected from, for example, excipients, adjuvants, diluents, fillers, or bulking agents, granulating agents, coating agents, release control agents, binding agents, disintegrants, lubricants, preservatives, antioxidants, buffers, suspending agents, thickeners, taste masking agents, stabilizers, or other carriers used in pharmaceutical compositions.

Examples of carriers include, but are not limited to, carboxymethylcellulose (CMC), phosphate buffered saline (PBS), water, emulsifier (such as oil and water emulsifier), or wetting agent.

According to the present invention, the drug can be formulated into a form suitable for parenteral administration. In the case of parenteral administration, the drug can be modified for intravenous, intramuscular, intraperitoneal, subcutaneous administration, or direct injection, infusion, or other methods reaching the target organs or tissues.

According to the present invention, amniotic fluid stem cells used for the treatment of urinary incontinence can be co-administered with another drug for the treatment of urinary incontinence to form a combination therapy.

The term "combination therapy" used herein refers to the separate or co-administration of multiple drugs. The doses of these drugs may be different from each other, and they may be administered at the same time or sequentially. In combination therapy, the route of administration of two or more drugs may be different, for example, one of them is parenteral administration and the other is oral administration.

Specifically, the drug disclosed in the present invention can form a combination therapy with the following drugs: anti-parasympathetic drugs, such as oxybutynin, tolterodine, propiverine, solifenacin, darifenacin, trospium, and fesoterodine; β-3 agonist, such as mirabegron; neurotoxin, such as onabutolinumtoxin A; or antidepressants, such as imipramine, duloxetine, ephedrine, and pseudoephedrine.

The present invention provides use of amniotic fluid stem cells for the manufacture of a medicament for the treatment of urinary incontinence.

The present invention also provides a method for treatment of urinary incontinence, comprising administering to a subject in need a therapeutically effective amount of amniotic fluid stem cells.

The present invention also provides a pharmaceutical composition for treatment of urinary incontinence, comprising amniotic fluid stem cells.

According to the present invention, the aforementioned treatment of urinary incontinence includes the treatment of urge incontinence, stress incontinence, overflow incontinence, functional incontinence, or mixed incontinence.

According to the present invention, the aforementioned treatment of urinary incontinence includes the treatment of overactive bladder or interstitial cystitis.

According to the present invention, the composition comprising amniotic fluid stem cells is suitable for parenteral administration.

In one embodiment, the pharmaceutical composition of the present invention comprises hyaluronic acid.

In one embodiment, the amniotic fluid stem cells are amniotic fluid stem cell spheroids.

In one embodiment, the pharmaceutical composition of the present invention comprises a pharmaceutically acceptable carrier.

In one embodiment, the dosage of the present invention is 500-50,000 amniotic fluid stem cells/μl.

In one embodiment, each of the amniotic fluid stem cell spheroids comprises 50-250 amniotic fluid stem cells.

Example 1 Treatment of Animals Suffering from Urinary Incontinence with the Composition of the Present Invention 1. Materials and Methods 1.1 Animals Six (6) to 8-week-old SD female rats purchased from BioLASCO Taiwan Co., Ltd., with an average weight of 200-300 grams (g) were used for the experiment. The rats were maintained in an animal facility on a 12-hour photoperiod, at a constant temperature (23±2° C.), with sufficient food and water supply.

1.2 Cells

Human amniotic fluid samples were obtained from women at 16 to 18 weeks of pregnancy. The acquisition of amniotic fluid samples was approved by the Clinical Trail Committee. Amniotic fluid stem cells were cultured from the obtained samples of 3-5 milliliters (ml) of amniotic fluid by a process that meets the requirements of clinical trials, and cell banks were established and stored in liquid nitrogen.

The method of separating and culturing amniotic fluid stem cells includes the following steps:

Human pregnant women at 16 to 22 weeks of pregnancy undergo routine prenatal examinations by amniocentesis. Amniotic fluid stem cells can be isolated and cultured from the extracted amniotic fluid. Fresh amniotic fluid or the upper layer fluid of amniotic fluid cells collected from a two-stage culture is cultured in a mesenchymal stem cell medium after the cells are generally centrifuged (for example, 150 g, 10 minutes) and precipitated.

Attached growth of amniotic fluid stem cell colonies can be observed after 5 to 10 days of culture. After trypsin treatment, subculture, and expansion culture, the attached cells with consistent morphology and similar to fibroblasts can be obtained. Cellular immunophenotype analysis showed >95% for CD29, CD44, CD73, CD90, and CD105, and <5% for CD45, CD34, CD14, CD19, and HLA-DR. The expression ratio of the cell surface markers of amniotic fluid stem cells is disclosed in Table 1 and FIG. 1. In addition, the cell surface markers of the amniotic fluid stem cells conform to those of mesenchymal stem cells and express the characteristics of neural stem cells, including cell surface markers nestin and sox2.

TABLE 1

| Surface Markers | Proportion of cells with positive surface markers (%) Amniotic fluid stem cells |
|---|---|
| Negative* | 0.68 |
| CD105 | 91.4 |
| CD73 | 98.4 |
| CD90 | 98.4 |
| CD44 | 99.8 |
| HLA-ABC | 99.9 |
| Nestin | 99.1 |
| Sox2 | 78.0 |

*Negative means that the cells do not express CD45, CD34, CD31, CD19, CD11b, HLA-DR.

1.3 Preparation of Amniotic Fluid Stem Cell Spheroids $1 \times 10^5$ amniotic fluid stem cells were inoculated in a culture plate that helps form cell spheroids (AggreWell). After culturing overnight, the cells formed spheroids, and each spheroid contained 100-200 cells. Amniotic fluid stem cells at a concentration of $1 \times 10^5$ cells/well were inoculated on a low-adherence culture plate, such as Aggrewell plate (StemCell Technologies) or a culture plate container that provides low-adherence. After culturing overnight, the cells formed spheroids, and each spheroid contained 100-200 cells.

1.4 Producing Experimental Animals with Urethral Sphincter Deficiency

The animals used in this embodiment were divided into a test group (urethral sphincter deficiency) and a control group (sham surgery group).

In the test group, the rats under general anesthesia were incised along the midline of the lower abdomen to expose the bladder and urethra. The perineal nerve located close to the veins of the thigh was found and cut off. The animals of the urinary incontinence operation group were sutured after the operation of urethral sphincter deficiency.

The animals of the control group were sutured after only undergoing a midline incision of the lower abdomen, without cutting off the perineal nerve (4 animals in this group).

1.5 Injection of Human Amniotic Fluid Stem Cells and Hyaluronic Acid

The groups used to test amniotic fluid stem cells in this example include:

(1) PBS injection group: The animals with urethral sphincter deficiency were injected with 10 microliters (μl) of PBS buffer in the 3 o'clock and 9 o'clock directions of the external sphincter muscle of urethra, respectively, as a control group without injection of amniotic fluid stem cells (6 animals in this group).

(2) Hyaluronic acid injection group: The animals with urethral sphincter deficiency were injected with 10 μl of hyaluronic acid in the 3 o'clock and 9 o'clock directions of the external sphincter muscle of urethra, respectively (6 animals in this group).

(3) Amniotic fluid stem cells and PBS injection group: During the operation causing urethral sphincter deficiency, the test animals were injected with 10 μl of PBS buffer containing about $1 \times 10^4$, $1 \times 10^5$, and $1 \times 10^6$ undifferentiated amniotic fluid stem cells in the 3 o'clock and 9 o'clock directions of the external sphincter muscle of urethra, respectively (20 μl in total) (6 animals in one group and totally 18 animals for 3 groups).

(4) Amniotic fluid stem cells and hyaluronic acid injection group: The animals with urethral sphincter deficiency were injected with 10 μl of hyaluronic acid pre-mixed with amniotic fluid stem cells in each of the 3 o'clock and 9 o'clock directions of the external sphincter muscle of urethra, respectively; wherein a total of about 1×10⁵ undifferentiated amniotic fluid stem cells were suspended in 20 μl of hyaluronic acid (6 animals in this group).

(5) Amniotic fluid stem cell spheroids injection group: The animals with urethral sphincter deficiency were injected with 10 μl of PBS pre-mixed with amniotic fluid stem cell spheroids in the 3 o'clock and 9 o'clock directions of the external sphincter muscle of urethra, respectively; wherein a total of about 1×10⁵ undifferentiated amniotic fluid stem cells were suspended in 20 μl of PBS (6 animals in this group).

(6) Amniotic fluid stem cell spheroids and hyaluronic acid injection group: The animals with urethral sphincter deficiency were injected with 10 μl of hyaluronic acid pre-mixed with amniotic fluid stem cell spheroids in the 3 o'clock and 9 o'clock directions of the external sphincter muscle of urethra, respectively; wherein a total of about 1×10⁵ undifferentiated amniotic fluid stem cells were suspended in 20 μl of hyaluronic acid (6 animals in this group).

1.6 Measurement of Leak Point Pressure (LPP)

Four weeks after the injection of amniotic fluid stem cells, the test animals were generally anesthetized with ether to avoid muscle relaxation. The pressure of the bladder leak point and the atresia point of the test animals were measured. A bladder catheter (PE-25) was inserted through the urethral orifice, and then the rat was placed on an inclined table and placed in a vertical position. The pressure in the bladder was connected to the bladder catheter and a pressure sensor through a 50 ml syringe, using a PE-50 tubing and a three-way stopcock. The pressure in the bladder was increased to the extent of visual recognition point of leakage (initiation of urine leakage). The pressure at this leak point is called the leak point pressure (LPP), and the average pressure of three leak points continuously measured was used as the data of the bladder function atlas of each animal.

1.7 Statistics

The results are shown as the average of the actual measured values, and the average plus or minus standard error (mean±SEM) is used as the basis for plotting graphs. The original data were analyzed with one-way ANOVA using GraphPad Prism for Windows to show the difference between the groups (* $p<0.05$; *** $p<0.001$).

2. Results 2.1 Test Results of Leak Point Pressure

Figure 2:
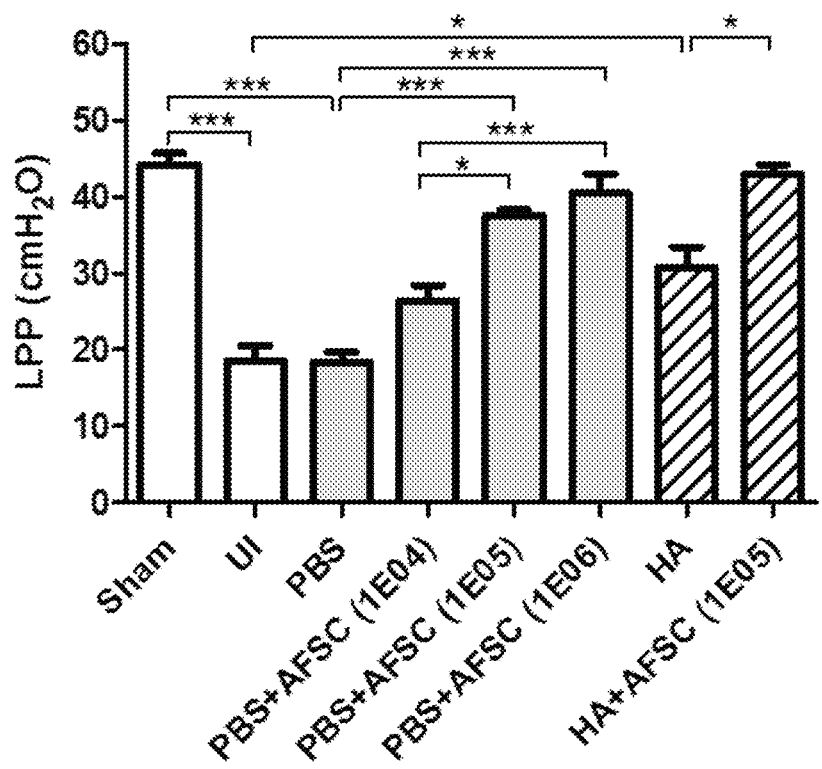
FIG. 2 shows the comparison of the leak point pressure of the rats with urinary incontinence transplanted with amniotic fluid stem cells. The doses of amniotic fluid stem cells were $1\times10^4$, $1\times10^5$, $1\times10^6/20$ µl vehicle, respectively; Sham: control group (sham surgery group); UI: Surgery-induced urethral sphincter deficiency group; AFSC: amniotic fluid stem cells; HA: hyaluronic acid.

By cutting the perineal nerve, the animal model of urinary incontinence in rats was successfully established. The leak point pressure of the test group (after cutting the perineal nerve, immediately suture the wound or suture the wound after injecting 20 μl of PBS) was 41.8% (UI) and 41.6% (PBS) of the control group (sham), respectively (FIG. 2).

Injection or transplantation of amniotic fluid stem cells (AFSCs) into the paraurethral sphincter of a rat reduces the level of urinary incontinence, with a dose-dependent effect and a statistical significance ($p<0.05$). The leak point pressure of the groups injected with 1×10⁴, 1×10⁵, and 1×10⁶ cells were 59.6%, 85.0%, 91.6% of the control group (sham), respectively. The leak point pressure of the animals transplanted with 1×10⁵ amniotic fluid stem cells mixed with hyaluronic acid onto the sphincter restored to 97.3% of the control group (sham) (FIG. 2).

Figure 3:
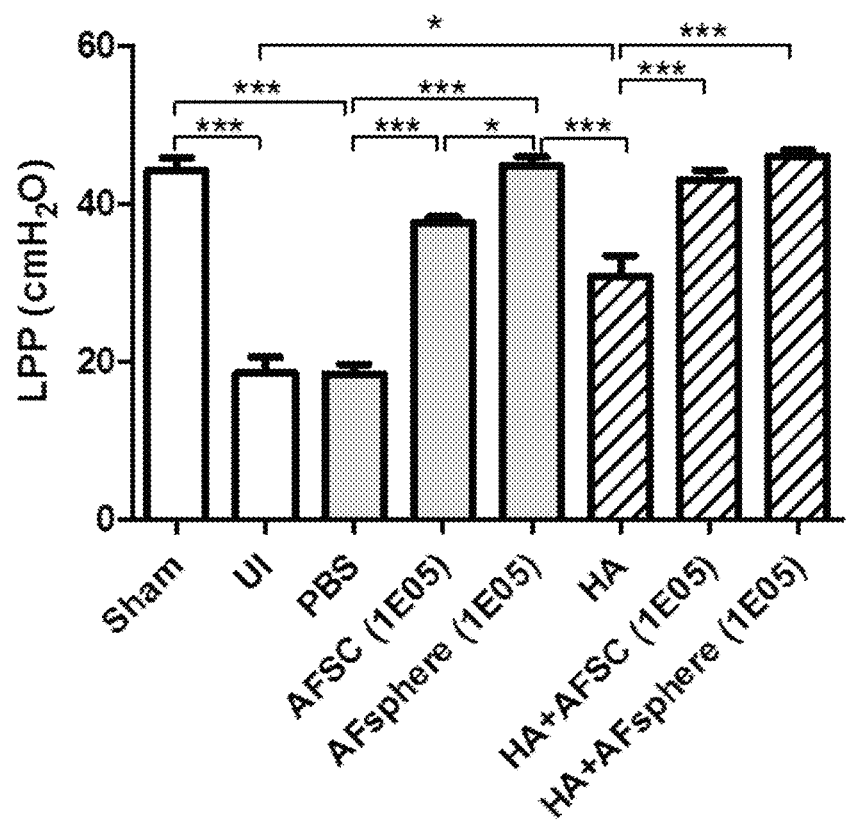
FIG. 3 shows the comparison of the leak point pressure of the rats with urinary incontinence transplanted with amniotic fluid stem cell spheroids. The doses of amniotic fluid stem cells were $1\times10^4$, $1\times10^5$, $1\times10^6/20$ µl vehicle, respectively; Sham: control group (sham surgery group); UI: surgery-induced urethral sphincter deficiency group; AFSC: amniotic fluid stem cells; AFsphere: amniotic fluid stem cell spheroids; HA: hyaluronic acid.

Under the same cell count, transplantation of amniotic fluid stem cell spheroids (AFsphere) formed by 1×10⁵ amniotic fluid stem cells has a more significant effect on reducing urinary incontinence than transplantation of individual stem cells. The leak point pressures of the group transplanted with stem cell spheroids and the group transplanted with individual stem cells (non-stem cell spheroids) were 101.3% and 85.0% of the control group, respectively (FIG. 3). The group transplanted with stem cell spheroids formed by 1×10⁵ amniotic fluid stem cells mixed with hyaluronic acid has a higher leak point pressure (104.2% of the control group), and has better results compared to the group transplanted with individual amniotic fluid stem cells mixed with hyaluronic acid (97.3% of the control group) (FIG. 3).

While preferred embodiments of the present invention have been shown and described herein, it will be obvious to those skilled in the art that such embodiments are provided by way of example only and can be implemented in combinations. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A method for the treatment of urinary incontinence with urethral sphincter deficiency, comprising administering to a subject in need thereof a pharmaceutical composition including a therapeutically effective amount of amniotic fluid stem cell spheroids and hyaluronic acid, wherein the pharmaceutical composition is administered by intramuscular injection to a sphincter muscle of urethra of the subject, and wherein the amniotic fluid stem cell spheroids are prepared by a method comprising inoculating amniotic fluid stem cells at a concentration of 1×10⁵ cells/well on a low-adherence culture plate, and culturing overnight to obtain the amniotic fluid stem cell spheroids, each containing 100-200 cells.

2. The method of claim 1, wherein the therapeutically effective amount is 500-50,000 amniotic fluid stem cells/μl.

* * * * *